US010524793B2

(12) United States Patent
De Rezende Neto

(10) Patent No.: US 10,524,793 B2
(45) Date of Patent: Jan. 7, 2020

(54) DEVICE FOR MANAGEMENT OF AN OPEN ABDOMEN

(71) Applicant: St. Michael's Hospital, Toronto (CA)

(72) Inventor: João Baptista De Rezende Neto, Toronto (CA)

(73) Assignee: St. Michael's Hospital, Toronto (CA)

( * ) Notice: Subject to any disclaimer, the term of this patent is extended or adjusted under 35 U.S.C. 154(b) by 216 days.

(21) Appl. No.: 15/550,444

(22) PCT Filed: Feb. 11, 2016

(86) PCT No.: PCT/CA2016/050124
§ 371 (c)(1),
(2) Date: Aug. 11, 2017

(87) PCT Pub. No.: WO2016/127256
PCT Pub. Date: Aug. 18, 2016

(65) Prior Publication Data
US 2018/0036006 A1    Feb. 8, 2018

Related U.S. Application Data

(60) Provisional application No. 62/115,932, filed on Feb. 13, 2015.

(51) Int. Cl.
*A61B 17/08*    (2006.01)
(52) U.S. Cl.
CPC ...... *A61B 17/085* (2013.01); *A61B 2017/081* (2013.01); *A61B 2017/086* (2013.01)
(58) Field of Classification Search
CPC ..... A61B 17/08; A61B 17/085; A61B 17/132; A61B 17/1322; A61B 17/1325;
(Continued)

(56) References Cited

U.S. PATENT DOCUMENTS 345,541 A * 7/1886 Reichardt ............ A61B 17/085
606/216
5,176,703 A * 1/1993 Peterson ............. A61B 17/085
602/41
(Continued)

FOREIGN PATENT DOCUMENTS

CN    101129273 A    2/2008
CN    202288560 U    7/2012
(Continued)

OTHER PUBLICATIONS

Kreis et al.; "Open abdomen management: A review of its history and a proposed management algorithm"; Med Sci Monit; 2013; 524-533; vol. 19.
(Continued)

*Primary Examiner* — Ryan J. Severson
(74) *Attorney, Agent, or Firm* — The Webb Law Firm

(57) ABSTRACT

A device for management of an open abdomen includes a belt having first and second end portions. The belt is positionable to extend partially around a patient's torso in a taut configuration with the end portions positioned on opposed sides of an incision in the patient's abdomen. A first connector is at the first end portion and a second connector is at the second end portion. The connectors are positionable adjacent each other on the opposed sides of the incision. At least one cinching device is connected to and extends between the connectors. The cinching device is positionable to extend over the incision when the connectors are positioned adjacent each other on opposed sides of the incision. The cinching device is adjustable to cinch the end portions towards each other to hold the incision in an at least partially closed position.

27 Claims, 15 Drawing Sheets

(58) Field of Classification Search
CPC .......... A61B 17/1327; A61B 2017/081; A61B 2017/086; A61B 2017/088
See application file for complete search history.

(56) References Cited

U.S. PATENT DOCUMENTS

| | | | |
|---|---|---|---|
| 5,533,963 A | 7/1996 | Hall | |
| 5,534,010 A * | 7/1996 | Peterson | A61B 17/085 606/215 |
| 5,665,108 A * | 9/1997 | Galindo | A61B 17/085 606/215 |
| 7,361,185 B2 * | 4/2008 | O'Malley | A61B 17/02 606/215 |
| 7,429,265 B2 * | 9/2008 | O'Malley | A61B 17/08 606/213 |
| 8,211,129 B2 * | 7/2012 | Regadas | A61B 17/1114 606/153 |
| 8,518,077 B2 * | 8/2013 | O'Malley | A61B 17/08 606/213 |
| 8,663,275 B2 * | 3/2014 | O'Malley | A61B 17/02 606/216 |
| 8,721,629 B2 * | 5/2014 | Hardman | A61B 17/085 604/543 |
| 8,920,351 B2 * | 12/2014 | Polliack | A61F 5/05883 128/96.1 |
| 8,926,536 B2 * | 1/2015 | Hopman | A61B 17/135 602/13 |
| 9,028,435 B2 * | 5/2015 | Hopman | A61B 17/1322 602/23 |
| 9,345,483 B1 * | 5/2016 | Sanders | A61B 17/083 |
| 9,427,238 B2 * | 8/2016 | Hopman | A61B 17/1325 |
| 9,526,502 B2 * | 12/2016 | Regadas | A61B 17/1114 |
| 9,757,131 B2 * | 9/2017 | Sanders | A61B 17/085 |
| 10,034,791 B2 * | 7/2018 | DeLuke | A61F 5/024 |
| 10,123,801 B2 * | 11/2018 | Belson | A61B 17/085 |
| 10,182,934 B2 * | 1/2019 | Hopman | A61F 5/0193 |
| 10,258,347 B2 * | 4/2019 | Hopman | A61B 17/1322 |
| 2003/0092969 A1 | 5/2003 | O'Malley et al. | |
| 2003/0163160 A1 * | 8/2003 | O'Malley | A61B 17/08 606/213 |
| 2006/0064125 A1 * | 3/2006 | Henderson | A61B 17/02 606/215 |
| 2008/0147115 A1 * | 6/2008 | O'Malley | A61B 17/02 606/216 |
| 2008/0312685 A1 * | 12/2008 | O'Malley | A61B 17/08 606/216 |
| 2009/0281560 A1 | 11/2009 | Wexner et al. | |
| 2010/0152770 A1 * | 6/2010 | Spencer | A61B 17/1325 606/203 |
| 2011/0137342 A1 * | 6/2011 | Henderson | A61B 17/02 606/232 |
| 2011/0152900 A1 * | 6/2011 | Regadas | A61B 17/1114 606/153 |
| 2013/0041303 A1 * | 2/2013 | Hopman | A61B 17/1322 602/23 |
| 2013/0110019 A1 * | 5/2013 | Hopman | A61B 17/135 602/13 |
| 2013/0310872 A1 * | 11/2013 | Croushorn | A61B 17/1325 606/202 |
| 2014/0155797 A1 * | 6/2014 | Hopman | A61F 5/0193 602/19 |
| 2015/0051530 A1 * | 2/2015 | Noda | A61B 17/08 602/41 |
| 2015/0119780 A1 * | 4/2015 | DeLuke | A61F 5/024 602/19 |
| 2017/0035422 A1 * | 2/2017 | Belson | A61B 17/085 |
| 2017/0240327 A1 * | 8/2017 | Sanders | A61B 17/08 |
| 2018/0036006 A1 * | 2/2018 | De Rezende Neto | A61B 17/085 |
| 2019/0076145 A1 * | 3/2019 | Belson | A61B 17/085 |

FOREIGN PATENT DOCUMENTS

| | | |
|---|---|---|
| CN | 202761509 U | 3/2013 |
| CN | 202950716 U | 5/2013 |
| TW | M494588 U | 2/2015 |

OTHER PUBLICATIONS

Maclean et al.; "Management Strategies for the Open Abdomen: Survey of the American Association for the Surgery of Trauma Membership"; Acta chir belg; 2008; pp. 212-222; vol. 108.

Mukhi et al.; "Management of the open abdomen using combination therapy with ABRA and ABThera systems"; J can chir; 2014; pp. 314-316; vol. 57:5.

* cited by examiner

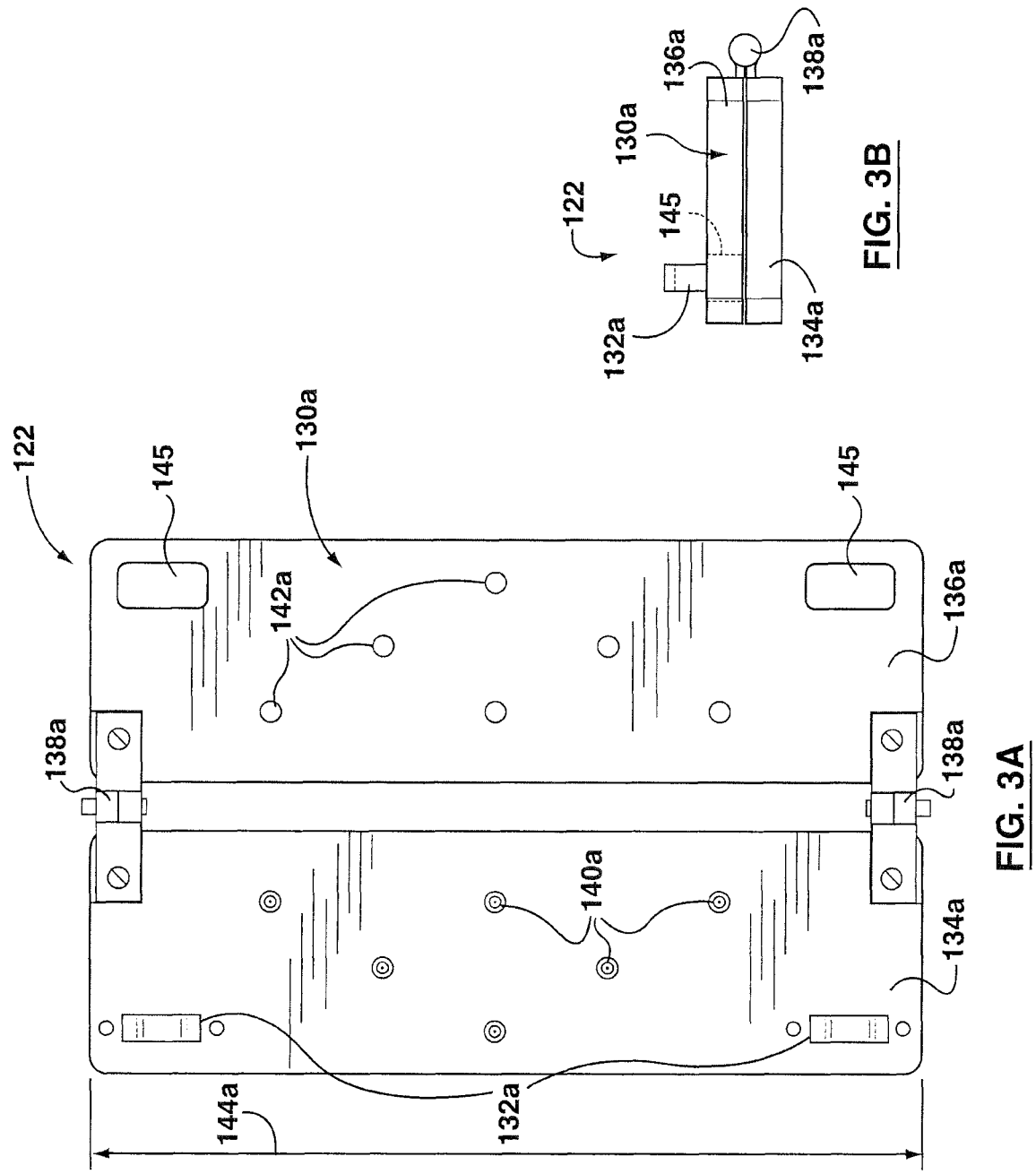

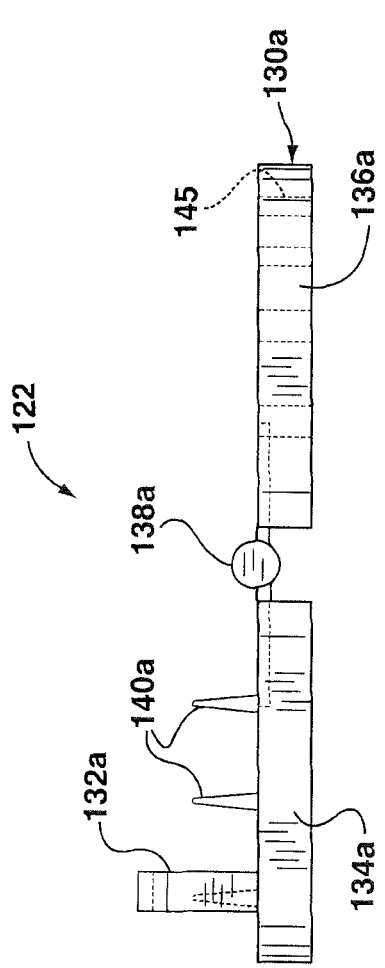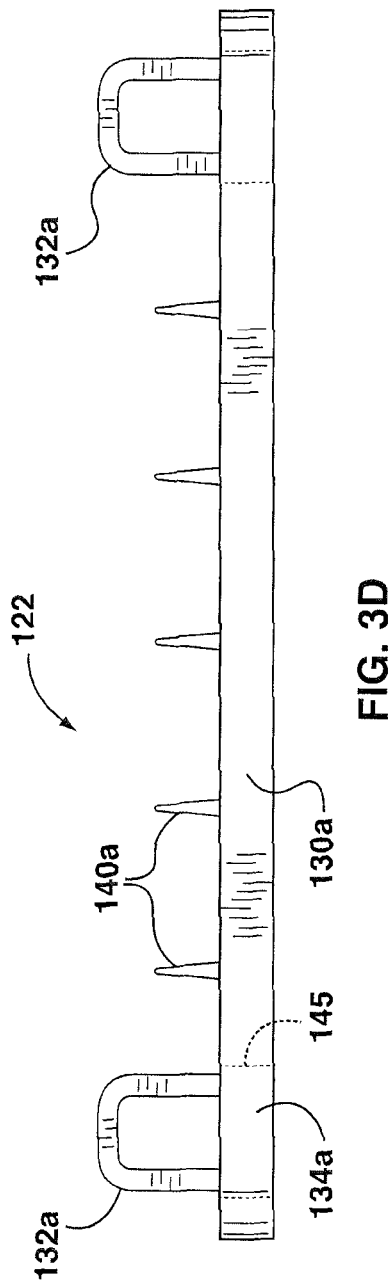

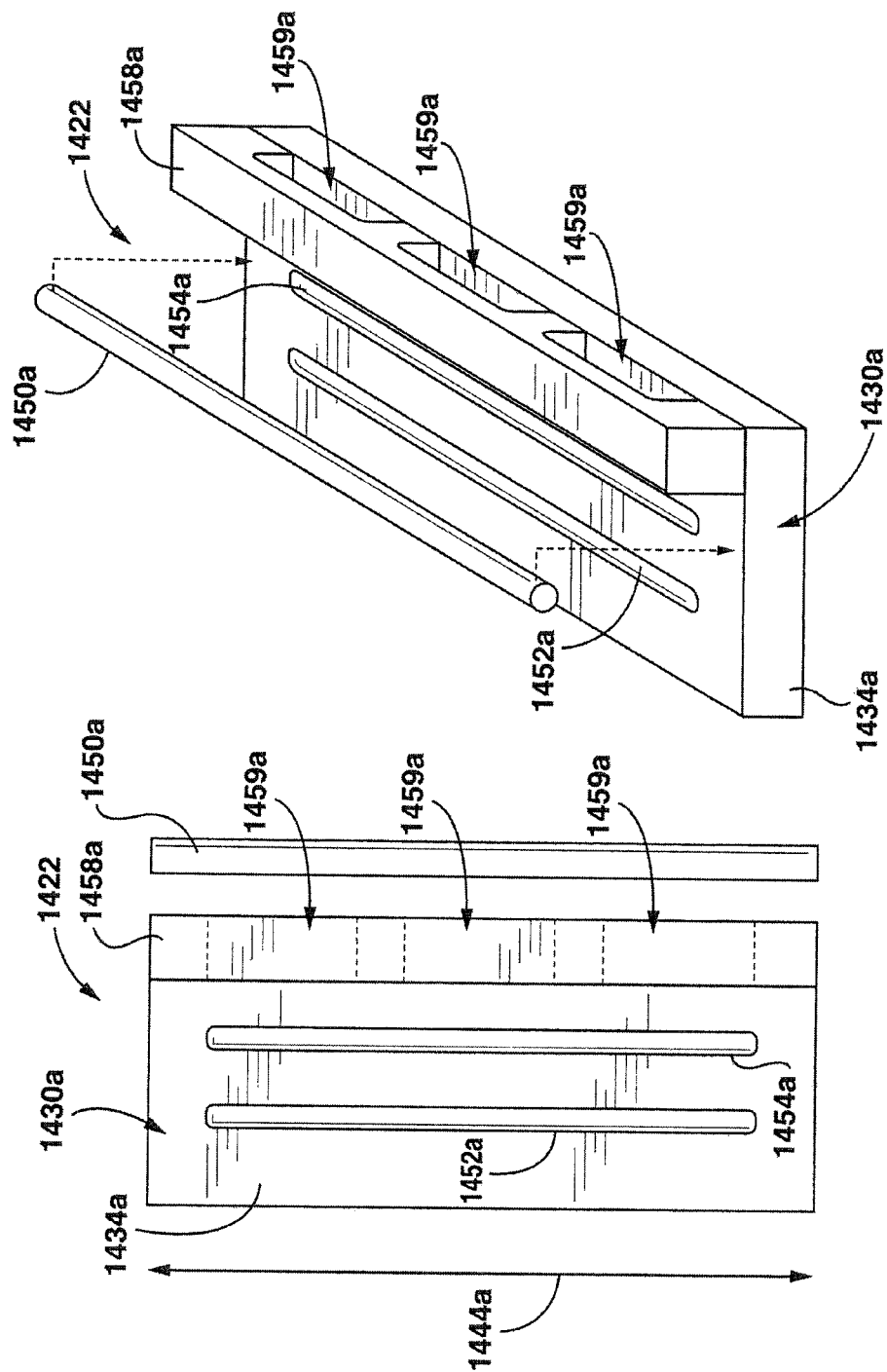

DEVICE FOR MANAGEMENT OF AN OPEN ABDOMEN

CROSS-REFERENCE TO RELATED APPLICATIONS

This application is the United States national phase of International Application No. PCT/CA2016/050124 filed Feb. 11, 2016, and claims benefit of U.S. Provisional Patent Application No. 62/115,932 filed Feb. 13, 2015, the disclosures of which are hereby incorporated in their entirety by reference.

FIELD

The disclosure relates to devices and related kits and methods for management of an open abdomen, which may occur, for example, after abdominal surgery. More specifically, the disclosure relates to devices, kits, and methods for holding an abdominal incision in an at least partially closed position.

BACKGROUND

Chinese Utility Model No. CN202288560U (Xu et al.) purports to disclose a support type belly fixing band, which comprises a netted belly protective sheet and a support waist protective sheet. The netted belly protective sheet and the support waist protective sheet are connected together through a highly elastic cord. The netted belly protective sheet is connected with a Velcro hook surface on the highly elastic cord, while the support waist protective sheet is connected with a Velcro rough surface on the highly elastic cord. The inner layer of the support waist protective sheet is provided with medical fiber plastic strips. The support type belly fixing band is purported to be simple in structure and easy to wear. Due to the adoption of the support type belly fixing band, the abdominal surgical incision of a patient is purported to be protected, while the waist of the patient is purported be supported at the same time. Meanwhile, the waist fatigue of the patient is purported to be relieved and the concrescence of the incision is purported to be effectively facilitated.

SUMMARY

The following summary is intended to introduce the reader to various aspects of the applicant's teaching, but not to define any invention.

According to one aspect, a device for management of an open abdomen is disclosed. The device comprises a belt having a first end portion and an opposed second end portion. The belt is positionable to extend partially around a patient's torso (e.g. around the posterior portion of the patient's torso) in a taut configuration with the first end portion and the second end portion positioned on opposed sides of an incision in the patient's abdomen. The device further comprises a first connector at the first end portion and a second connector at the second end portion. The first connector and second connector are positionable adjacent each other on the opposed sides of the incision when the belt is positioned around the patient's torso in the taut configuration. At least one cinching device is connected to and extends between the first connector and the second connector. The cinching device is positionable to extend over the incision when the first connector and second connector are positioned adjacent each other on opposed sides of the incision. The cinching device is adjustable to cinch the first end portion and second end portion towards each other to hold the incision in an at least partially closed position.

In some examples, the first connector may comprise (i) a first belt lock holding the first end portion, and (ii) a first loop connected to the first belt lock and connected to the cinching device. The second connector may comprise (i) a second belt lock holding the second end portion, and (ii) a second loop connected to the second belt lock and connected to the cinching device. In some examples, the first loop and second loop may be positionable to be spaced away from the patient's skin when the first belt lock and second belt lock are positioned on opposed sides of the incision.

In some examples, the first belt lock may have a first belt lock length extending transverse to the belt, and the first loop may extend along a majority of the first belt lock length. The second belt lock may have a second belt lock length extending transverse to the belt, and the second loop may extend along a majority of the second belt lock length.

In some examples, the first connector may comprise (i) a first belt lock holding the first end portion, wherein the first belt lock has a first belt lock length extending transverse to the belt, and (ii) a first set of loops connected to the first belt lock and connected to the at least one cinching device, wherein the first set of loops is spaced apart along the first belt lock length.

In some examples, the second connector may comprise (i) a second belt lock holding the first end portion, wherein the second belt lock has a second belt lock length extending transverse to the belt, and (ii) a second set of loops connected to the second belt lock and connected to the at least one cinching device, wherein the second set of loops is spaced apart along the second belt lock length. In some examples, the first set of loops and second set of loops may be positionable to be spaced away from the patient's skin when the first belt lock and second belt lock are positioned on opposed sides of the incision.

In some examples, the first belt lock may comprise a clamp holding the first end portion, and the second belt lock may comprise a clamp holding the second end portion.

In some examples, the first belt lock may comprise a plate having at least one slot extending therethrough, and at least one rod. The first end portion may comprise a fold threaded through the at least one slot. The rod may be positioned in the fold.

In some examples, the cinching device may be threaded through the first loop and the second loop.

In some examples, the cinching device may comprise a zip tie.

In some examples, the belt may comprise a surgical bandage.

In some examples, the device may further comprise a shim underneath one of the first connector and the second connector and positioning the one of the first connector and the second connector at an incline. The shim may be removable from the one of the first connector and the second connector.

According to another aspect, a method for management of an open abdomen is disclosed. The method comprises a) positioning a belt to extend partially around a patient's torso from a first position on a first side of an incision in the patient's abdomen, around the back of the patient, to a second position on a second side of the incision, in a taut configuration; b) cinching the belt to a cinched configuration to bring the first side of the incision and second side of the incision towards each other; and c) temporarily securing the belt in the cinched configuration, to temporarily hold the incision in an at least partially closed configuration.

In some examples, prior to step b), the method may further comprise securing a first connector to a first end portion of the belt, and securing a second connector to a second end portion of the belt.

In some examples, prior to step b), the method may further comprise positioning the first connector on the first side of the incision, and positioning the second connector on the second side of the incision adjacent the first connector.

In some examples, the method may further comprise inclining at least one of the first connector and the second connector with respect to the patient's abdomen. The inclining step may comprise positioning a shim underneath the one of the first connector and the second connector.

In some examples, prior to step b), the method may further comprise securing a cinching device to the first connector and second connector so that the cinching device extends between the first connector and the second connector and over the incision. The securing step may comprise securing a plurality of cinching devices to extend between the first connector and the second connector, wherein the plurality of cinching devices are spaced apart along the incision.

In some examples, step b) may comprise cinching the cinching device.

In some examples, step c) may be carried out automatically upon cinching the belt.

In some examples, the method may further comprise d) tightening the belt periodically.

In some examples, the steps a) to c) may be carried out without creating any wounds in the patient's abdomen.

In some examples, the method may further comprise containing and protecting the abdominal contents during steps a) to c).

According to another aspect, a kit of parts for a device for management of an open abdomen is disclosed. The kit of parts comprises a belt having a first end portion and an opposed second end portion. The belt is positionable to extend partially around a patient's torso in a taut configuration with the first end portion and the second end portion positioned on opposed sides of an incision in the patient's abdomen. The kit further comprises a first connector and a second connector. The first connector and second connector are positionable adjacent each other on the opposed sides of the incision when the first connector is connected to the first end portion and the second connector is connected to the second end portion and when the belt is positioned around the patient's torso in the taut configuration. The kit further comprises at least one cinching device. The cinching device is positionable to extend over the incision when connected to the first connector and second connector and when the first connector and second connector are positioned adjacent each other on opposed sides of the incision. The cinching device is adjustable to cinch the first end portion and second end portion towards each other to hold the incision in an at least partially closed configuration.

In some examples, the first connector, second connector, and belt may be separate pieces and may be provided unassembled to each other.

In some examples, the first connector, second connector, and belt may be separate pieces and may be provided assembled to each other.

In some examples, the kit may further include instructions for use.

In some examples, the cinching device may be a separate piece from the belt, the first connector, and the second connector, and may be provided unassembled to the belt, first connector, and second connector.

In some examples, the first connector may comprise (i) a first belt lock for holding the first end portion, and (ii) a first loop connectable to the first belt lock and connectable to the cinching device. The second connector may comprise (i) a second belt lock for holding the second end portion, and (ii) a second loop connectable to the second belt lock and connectable to the cinching device.

In some examples, the second belt lock may have a second belt lock length extending transverse to the belt. The second loop may extend along a majority of the second belt lock length.

In some examples, the first connector may comprise (i) a first belt lock for holding the first end portion, wherein the first belt lock has a first belt lock length, and (ii) a first set of loops connected to the first belt lock and connectable to the cinching device, wherein the first set of loops are spaced apart along the first belt lock length. The second connector may comprise (i) a second belt lock for holding the first end portion, wherein the second belt lock has a second belt lock length, and (ii) a second set of loops connected to the second belt lock and connected to the cinching device, wherein the second set of loops is spaced apart along the second belt lock length.

In some examples, the first belt lock may comprise a clamp for holding the first end portion, and the second belt lock may comprise a clamp for holding the second end portion.

In some examples, the cinching device may be threaded through the first loop and the second loop.

In some examples, the cinching device may comprise a zip tie.

In some examples, the belt may comprise a surgical bandage.

In some examples, the kit may further comprise at least one shim securable to one of the first connector and second connector to position the one of the first connector and the second connector at an incline with respect to the patient's abdomen.

According to another aspect, a device for management of an open abdomen is disclosed. The device comprises a belt having a first end portion and an opposed second end portion. The belt is positionable to extend partially around a patient's torso in a taut configuration with the first end portion and the second end portion positioned on opposed sides of an incision in the patient's abdomen. The device further comprises a first belt lock holding the first end portion and a second belt lock holding the second end portion. The first belt lock and second belt lock are positionable adjacent each other on the opposed sides of the incision when the belt is positioned around the patient's torso in the taut configuration. At least a first loop is connected to the first belt lock and a second loop is connected to the second belt lock. The first and second loops are positionable to be spaced away from the patient's skin when the first belt lock and second belt lock are positioned on opposed sides of the incision. A zip tie is threaded through the first loop and the second loop and is positionable to extend over the incision when the first belt lock and second belt lock are positioned adjacent each other on opposed sides of the incision. The zip tie is tightenable to cinch the first end portion and second end portion towards each other to hold the incision in an at least partially closed position.

BRIEF DESCRIPTION OF THE DRAWINGS

The drawings included herewith are for illustrating various examples of articles, methods, and apparatuses of the present specification and are not intended to limit the scope of what is taught in any way. In the drawings:

FIG. 3A is a top plan view of a first connector of the device of FIG. 2, in an open configuration;

FIG. 3B is a side view of the first connector of the device of FIG. 2, in a closed configuration;

FIG. 3C is a side view of the first connector of the device of FIG. 2, in an open configuration;

FIG. 3D is a front view of the first connector of the device of FIG. 2, in an open configuration;

FIG. 14A is a top plan view of another first connector of another kit of parts for a device for management of an open abdomen;

FIG. 14B is a perspective view of the first connector of FIG. 14A;

DETAILED DESCRIPTION

Figure 1:
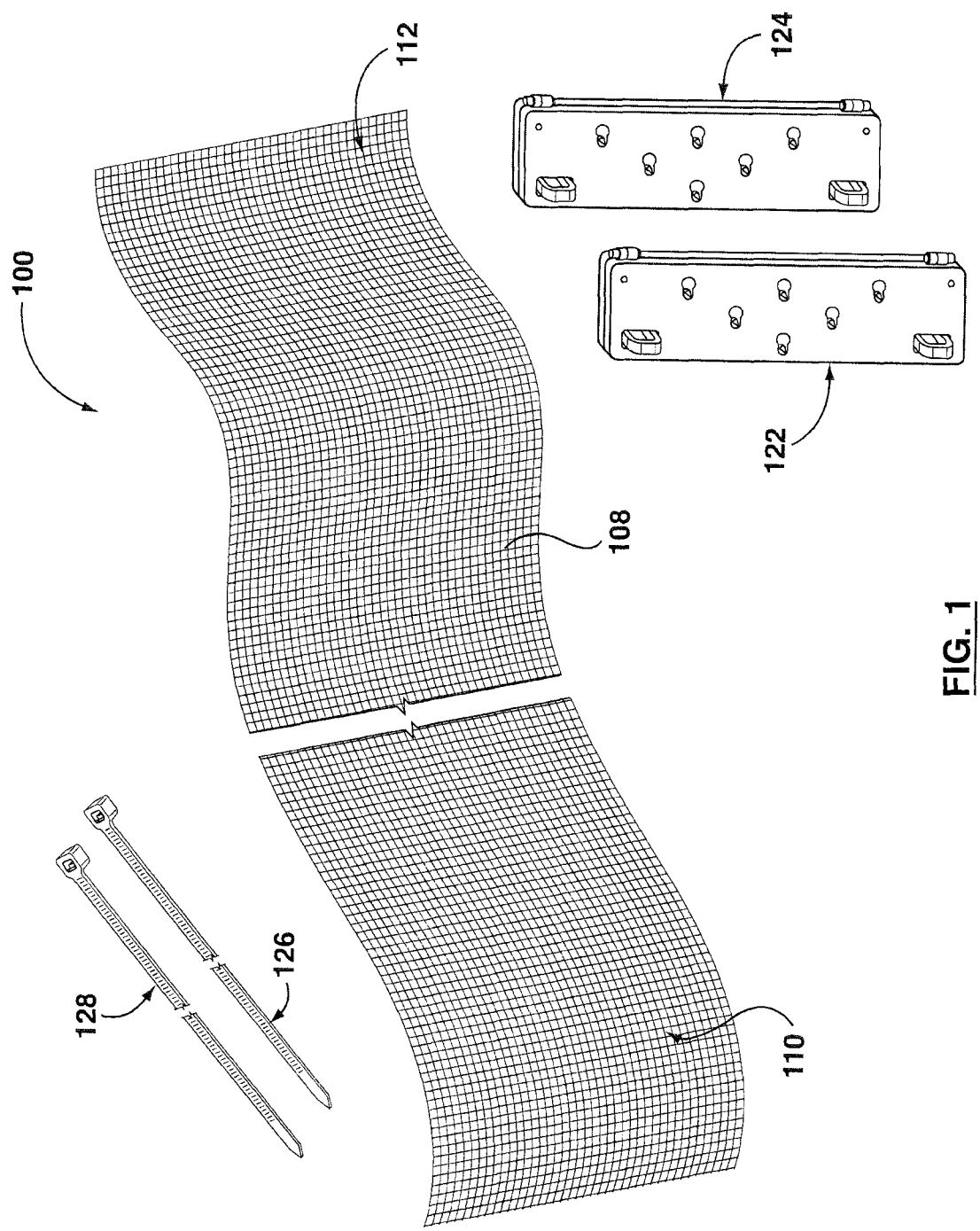
FIG. 1 is a perspective view showing a kit of parts for a device for management of an open abdomen, in an unassembled state.

Various apparatuses or processes will be described below to provide an example of an embodiment of the claimed subject matter. No embodiment described below limits any claim and any claim may cover processes or apparatuses that differ from those described below. The claims are not limited to apparatuses or processes having all of the features of any one apparatus or process described below or to features common to multiple or all of the apparatuses described below. It is possible that an apparatus or process described below is not an embodiment of any exclusive right granted by issuance of this patent application. Any invention disclosed in an apparatus or process described below and for which an exclusive right is not granted by issuance of this patent application may be the subject matter of another protective instrument, for example, a continuing patent application, and the applicants, inventors or owners do not intend to abandon, disclaim or dedicate to the public any such subject matter by its disclosure in this document.

Following many abdominal operations, the incision in the patient's abdomen is left open temporarily. This may be referred to as an "open abdomen". The incision may be left open, for example, for logistic reasons, technical reasons, or due to the patient's critical condition. The abdominal incision is typically closed at a later date, for example up to several days following the abdominal operation. There are several risks associated with an open abdomen, including an increased mortality rate, increased risk of infection, impaired abdominal wall function, respiratory complications, and enterocutaneous fistula. Furthermore, retraction of the wound edges may result in a loss of abdominal domain, which may ultimately impede successful definitive closure of the open abdomen.

Disclosed herein is a device and related kit and method for management of an open abdomen. The device may generally hold the abdominal incision in a closed or partially closed position, by wrapping or extending at least partially around the patient's torso (e.g. around the posterior portion of the patient's torso), and being cinched to bring the incision towards a closed position. In some examples, the device may bring the sides of the incision towards each other medially, and because the device wraps at least partially around the patient's torso, may also bring the abdominal wall muscles upwards. In some examples, the device may do so without touching the incision, and/or without requiring any additional wounds be created in the patient's abdomen, such as in the abdominal skin or fascia. For example, the device may in some instances be used without applying any stitches to the patient. As such, the device may optionally be applied at the bedside.

As used herein, the term "partially closed" indicates that the sides of the incision have been brought together medially (i.e. towards the midline), but are not in close enough contact to be definitively closed, for example with sutures. The term "closed" indicates that the sides of the incision have been brought together medially and are in close enough contact to be definitively closed, for example with sutures.

It is believed that the device, kit, and method may reduce one or more of the above-noted risks. It is further believed that the device, kit, and method may prevent or reduce the risk of the retraction of wound edges, thereby preventing or reducing the risk of the loss of abdominal domain. It is further believed that the device, kit, and method may increase the chance of successful definitive closure of the open abdomen.

Referring now to FIG. 1, an example kit of parts 100 for management of an open abdomen is shown. In FIG. 1, the parts 100 are shown in an unassembled configuration. The parts 100 may be assembled to form a device 102 for management of an open abdomen, shown in FIG. 2 in use on a patient 104 having an abdomen 106 that is open.

Figure 2:
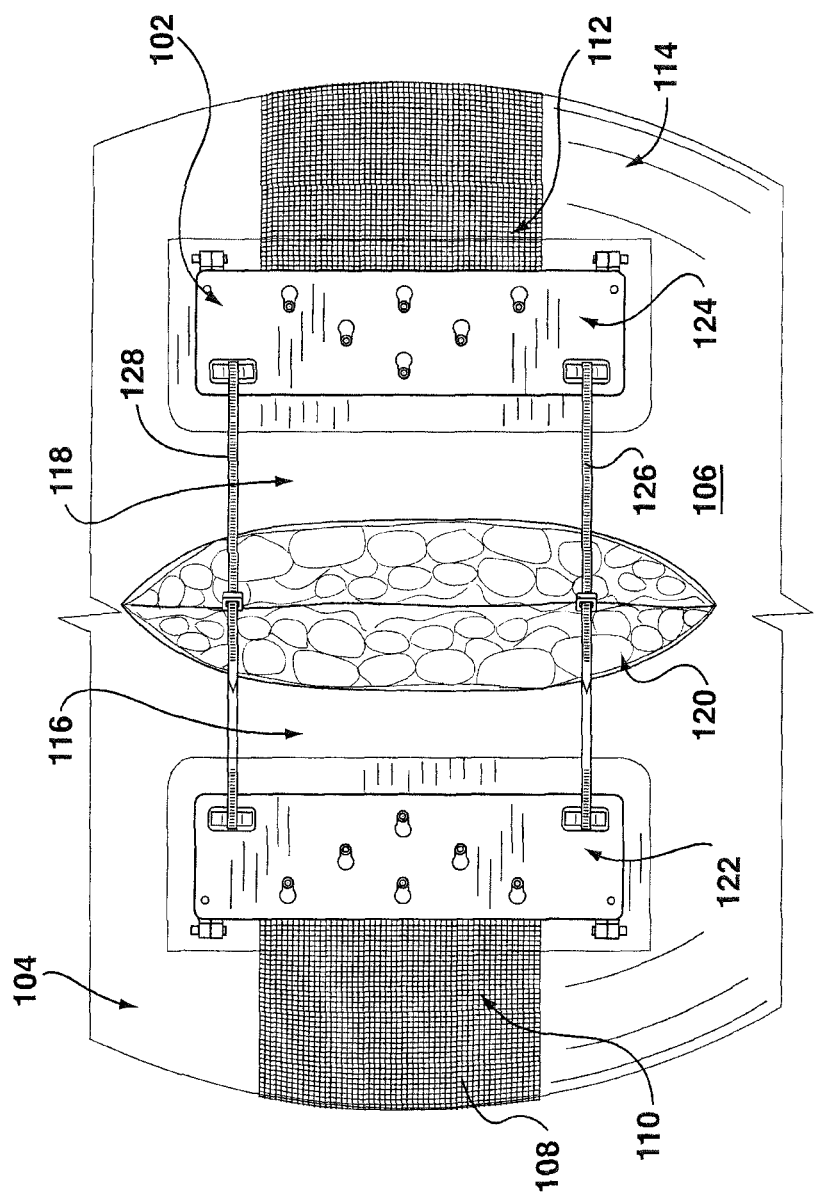
FIG. 2 is a top plan view showing the kit of parts of FIG. 1 assembled into a device for management of an open abdomen and in use on a patient having an open abdomen.

Referring still to FIG. 1, in the example shown, the kit 100 includes a belt 108 having a first end portion 110, and an opposed second end portion 112. Referring to FIG. 2, and as will be described in further detail below, the belt 108 is positionable to extend partially around a patient's torso 114 in a taut configuration with the first end portion 110 and the second end portion 112 positioned on opposed sides 116, 118, respectively, of an incision 120 in the patient's abdomen 106.

The belt 108 may be made from a variety of materials, including but not limited to woven fabrics, non-woven fabrics, non-fabric materials such as plastic films, synthetic materials, natural materials, or combinations thereof. Furthermore, the belt may be made from one piece of material, or may be made from more than one piece of material. Furthermore, the belt may be disposable, or may be reusable (i.e. may be sterilizable). In the example shown, the belt consists of a disposable woven surgical bandage.

Referring back to FIG. 1, the kit 100 further includes a first connector 122 and a second connector 124, for connecting the belt 108 to one or more cinching devices described below. Referring to FIG. 2, and as will be described in further detail below, when the device 102 is assembled, the first connector 122 is at the first end portion 110 of the belt 108, and the second connector is at the second end portion 112 of the belt. In use, the first connector 122 and second connector 124 are positionable adjacent each other on the opposed sides 116, 118 of the incision 120 when the belt 108 is positioned around the patient's torso 114 in the taut configuration.

In the example shown, the first connector 122, second connector 124, and belt 108 are separate pieces, and the first connector 122 and second connector 124 are provided unassembled to the belt 108. In alternative examples, the first connector 122, second connector 124, and/or the belt 108 may be provided assembled to each other. In further alternative examples, the first connector 122, second connector 124, and/or the belt 108 may be integrally formed.

Referring back to FIG. 1, the kit 100 may further include at least one cinching device for cinching the belt 108 and bringing the incision 120 towards a closed position. In the example shown, the kit includes two cinching devices, 126, 128. Referring to FIG. 2, as will be described in further detail below, when the device 102 is assembled, the cinching devices 126, 128 are connected to and extend between the first connector 122, and second connector 124. In use, the cinching devices 126, 128 are positionable to extend over the incision 120 when the first connector 122 and second connector are 124 positioned adjacent each other on opposed sides of the incision 120. The cinching devices 126, 128 are adjustable to cinch the first end portion 110 and second end portion 112 of the belt 108 towards each other to hold the incision 120 in an at least partially closed position.

In the example shown, each cinching device 126, 128 is a zip tie. Zip ties are known in the art, and will not be described in detail herein. The zip ties may be single use zip ties that may not readily be loosened or undone when cinched, or reusable zip ties that may be loosened. In alternative examples, the cinching devices may be another device that can be adjusted to bring the first end portion 110 of the belt 108 and the second end portion 112 of the belt 108 towards each other. For example, the cinching device may be a cord or cable that may be laced between the first 122 and second 124 connectors and tightened and tied.

Referring to FIGS. 3A to 3D, the first connector 122 will be described in further detail. The second connector 124 is generally identical to the first connector 122, and for simplicity, will not be described in detail herein. Furthermore, features of the first connector 122 will be referred to with the prefix "first", and reference numerals for the features of the first connector will end with the suffix "a". Similar features of the second connector 124 will be referred to herein with the prefix "second", and reference numerals for the features of the second connector will end with the suffix "b".

In the example shown, the first connector 122 includes a first belt lock 130a for holding and gripping the first end portion 110 of the belt 108, and a first set of loops 132a connected to the first belt lock 130a and connectable to the cinching devices 126, 128.

The first belt lock 130a is in the form of a clamp, and includes a pair of plates 134a, 136a, respectively, joined together by hinges 138a. The plates 134a, 136a may be pivoted towards and away from each other about the hinges 138a, to move the first connector 122 between an open position, shown in FIGS. 3A, 3C, and 3D, and a closed position, shown in FIG. 3B.

In the example shown, the first belt lock 130a includes a gripping mechanism to aid in firmly holding the belt 108. In the example shown the gripping mechanism includes a plurality of spikes 140a extending upwardly from the first plate 134a, and a plurality of openings 142a in the plate 136a, for receiving the spikes 140a when the first connector 122 is in the closed position.

In use, the first end portion 110 of the belt 108 may be placed between the plates 134a and 136a while the first connector 122 is in the open position. The plates 134a and 136a may then be moved towards each other, to the closed position, to sandwich the first end portion 110 of the belt therebetween. The spikes 140a will enter the openings 142a, and will grip the belt 108.

Referring to FIGS. 3A and 3D, the loops 132a extend upwardly from the plate 134a and are spaced apart along the length 144a of the first belt lock 130a (also referred to herein as the first belt lock length 144a). The plate 136a includes a set of apertures 145. As shown in FIG. 3B, when the first connector 122 is in the closed position, the loops 132a extend through the apertures 145, and upwardly beyond the plate 136a. The zip ties 126, 128 may be threaded through the loops 132a, in order to connect the zip ties 126, 128 to the loops 132a.

In alternative examples, the first connector may be of another configuration (examples of which are described below with respect to FIGS. 14A to 16). For example, the first belt lock may grip the belt in another way, and may not necessarily include plates and/or hinges. For further example, the number of loops and the number of apertures may vary (as described below with respect to FIG. 16).

In the example shown, when the zip ties 126, 128 are threaded through the loops 132a, the belt lock 130a is held in the closed position, since the loops extend from the plate 134a and through the apertures 145 in the plate 136a. In alternative examples, the belt lock 130a may be held in the closed position in another manner, for example via a separate clamping mechanism, and the loops 132a may extend upwardly from the plate 136a.

In some examples, the kit may include instructions for use of the device, for examples instructions for assembly of the device and/or instructions for applying the device to a patient.

In some examples, reusable parts of the device may be sold separately from single-use parts of the device. For example, the connectors 122, 124 may in some examples be sterilizable and reusable, and may be sold on their own. The belt 108 and cinching devices 126, 128 may be single-use, and may be sold together in a kit separately from the connectors 122, 124. Furthermore, hydrocolloid bandages 146 and gauze 148, as will be described further below, may optionally be included in the kit of single-use parts.

An example method for managing an open abdomen will presently be described with reference to the photographs of FIGS. 4 to 10. The method will be described with reference to device 102; however, in alternative examples, other devices may be used.

Figure 4:
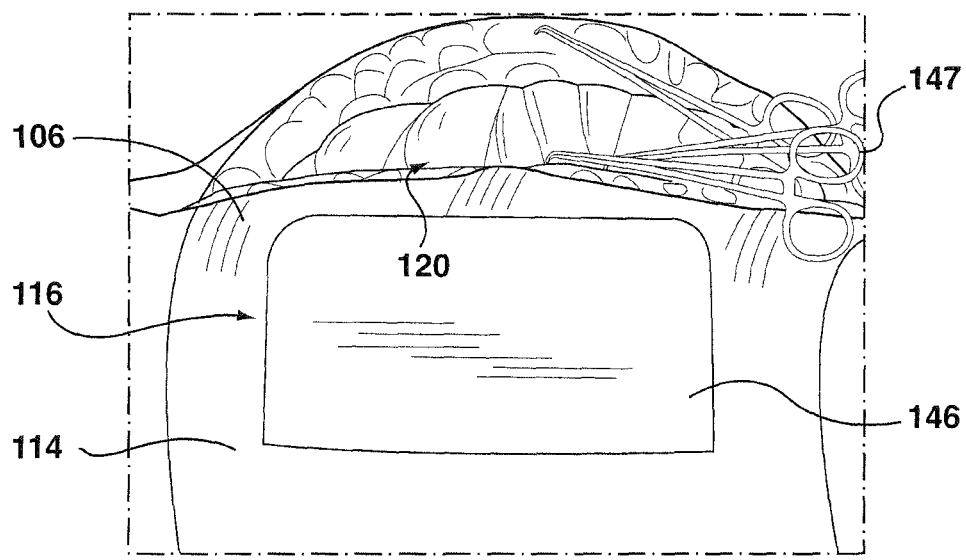
FIGS. 4 to 10 are a series of perspective views showing a series of steps for applying the device of FIG. 2 to a patient.

Referring to FIG. 4, the torso 114 of a patient having an open abdomen 106 is shown. In some examples, sutures may applied to the fascia of the incision 120, and may held in place with holders 147. The sutures may be tightened at a later date upon definitive closing of the incision 120. In alternative examples, these stitches may be omitted. Furthermore, in the example shown, hydrocolloid bandages 146 are placed opposed sides 116, 118 (only one side 116 is visible in FIG. 4) of the incision 120 to protect the skin, and a plastic film (not visible) was placed over the patient's bowel to protect the bowel. In alternative examples, the hydrocolloid bandage can be omitted, or replaced with another material suitable for protecting the skin from ulceration. In further alternative examples, the plastic film can be omitted or replaced by another non-adherent smooth surface material suitable to protect the bowel.

Figure 5:
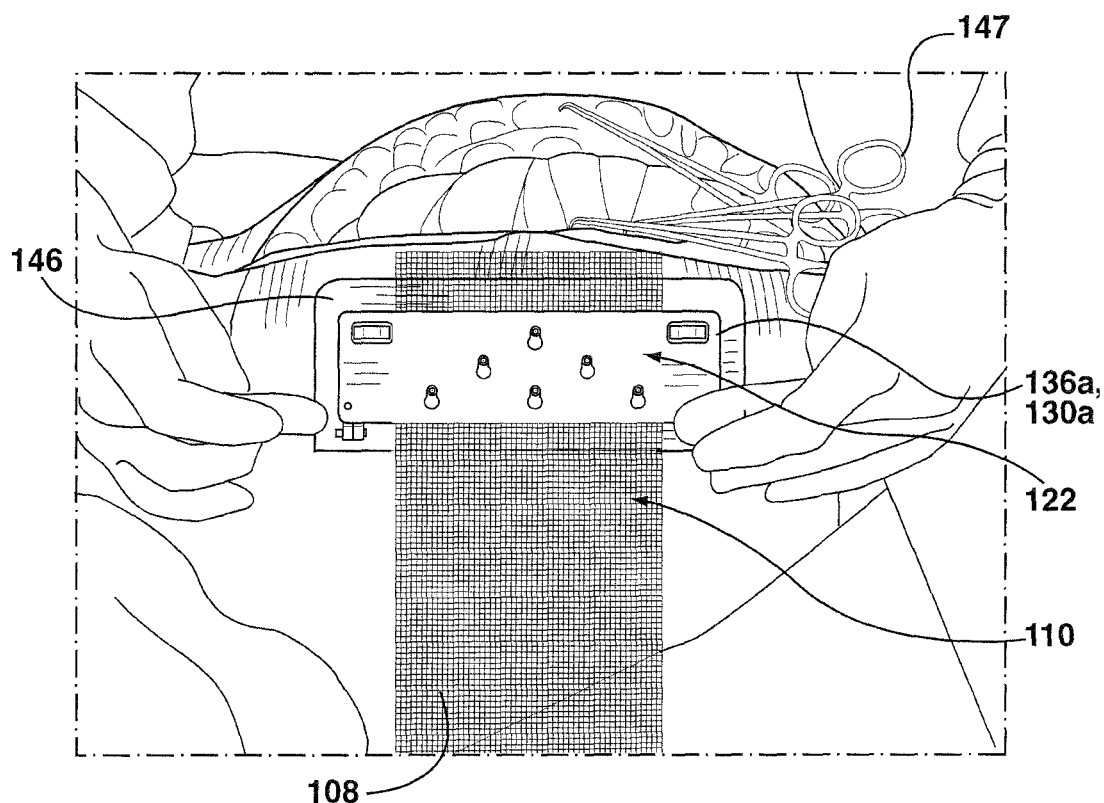

Referring to FIG. 5, the first connector 122 may be secured to the first end portion 110 of the belt 108, by positioning the first end portion 110 of the belt 108 between the plates 134a, 136a of the first belt lock 130a (only plate 134a is visible in FIG. 5) and moving the plates 134a, 136a to the closed position. The first connector 122 may then be positioned on the first side 116 of the incision 120 by laying the first connector 122 on the hydrocolloid bandage 146 on the first side 116 of the incision 120 so that the length 144a (not shown in FIG. 5) of the first belt lock 130a is generally parallel to the incision 120.

Figure 6:
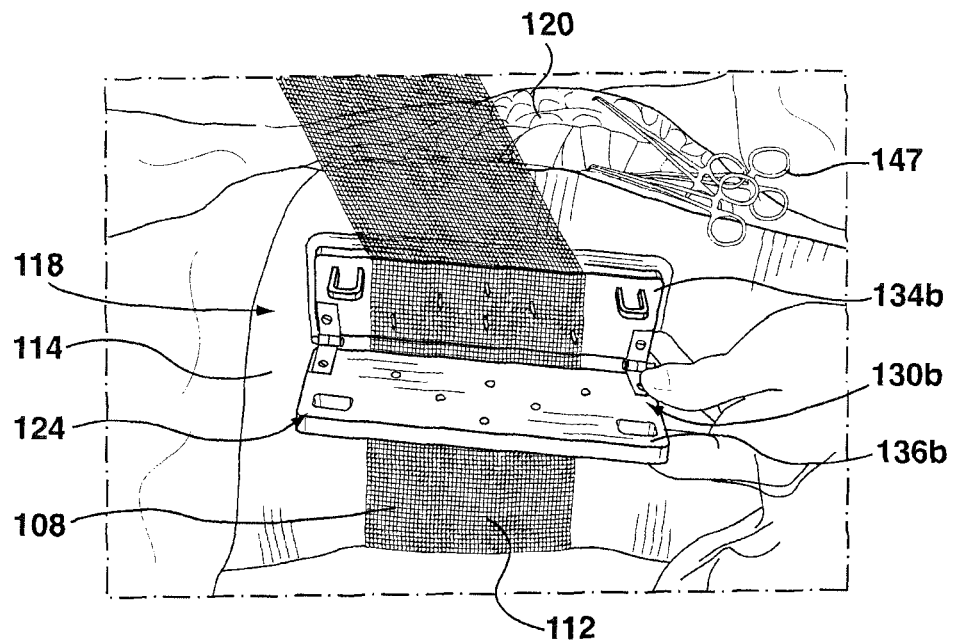
Figure 7:
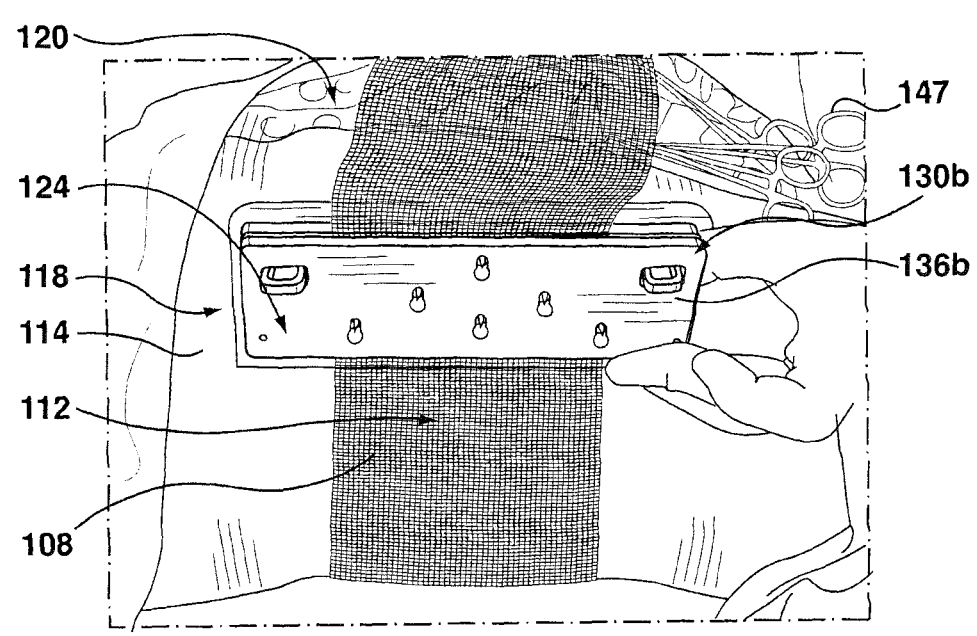

Referring to FIGS. 6 and 7, the belt 108 may then be positioned to extend partially around the patient's torso 114 from a first position on the first side 116 (not shown in FIGS. 6 and 7) of the incision 120 in the patient's abdomen 106, around the back of the patient, to a second position on the second side 118 of the incision 120, in a taut configuration. The second belt lock 130b of the second connector 124 may then be secured to the second end portion 112 of the belt 108, by sandwiching the second end portion 112 of the belt 108 between the plates 134b, 136b of the second belt lock 130b. The second connector 124 may then be positioned on the second side 118 of the incision 120 by laying the second connector 124 on the hydrocolloid bandage 146 on the second side 118 of the incision 120, so that the length of the second belt lock 130b is generally parallel to the incision 120, and the belt 108 is generally taut.

In some examples, excess length of the belt 108 may be trimmed from the belt after laying the first 122 and second 124 connectors on the hydrocolloid bandages.

Figure 8:
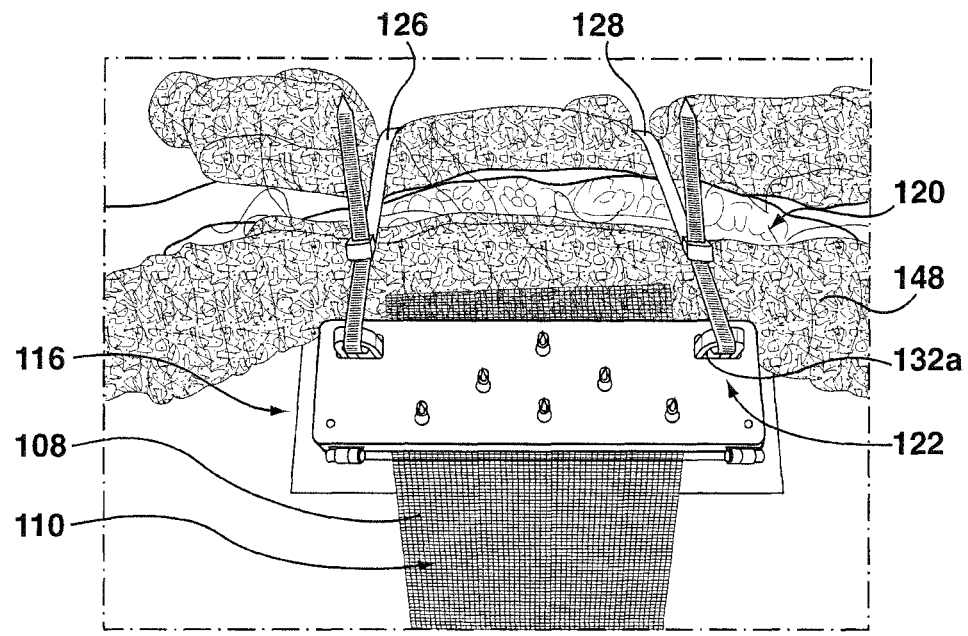
Figure 9:
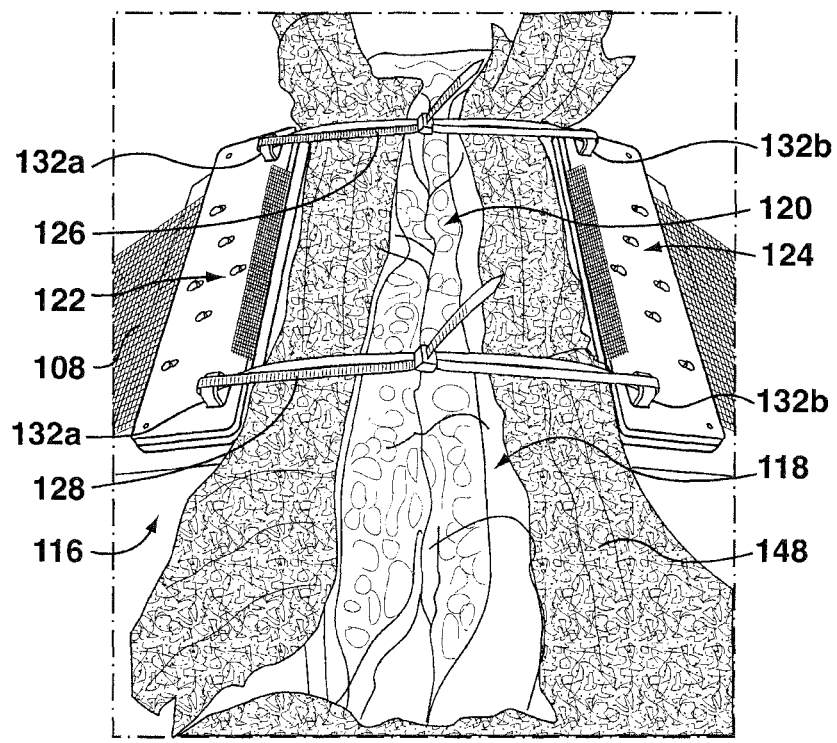

Referring to FIGS. 8 and 9, the belt 108 may then be cinched to a cinched configuration to bring the first side 116 of the incision 120 and second side 118 of the incision 120 towards each other. Specifically, two cinching devices 126, 128, which in this example are zip ties, may each be secured to the first connector 122 and second connector 124 to extend between the first connector 122 and the second connector 124 and over the incision 120. Each zip tie may be threaded through one of the loops 132a of the first connector 122 and one of the loops 132b of the second connector 124. Each zip tie may then be tightened to cinch the first end portion 110 of the belt 108 and second end portion 112 of the belt 108 towards each other, and bring the first side 116 of the incision 120 and second side 118 of the incision 120 towards each other.

The first 116 and second 118 sides of the incision 120 may in some examples be brought together so that they are in contact with each other (i.e. may be brought to a closed position). In other examples, the first 116 and second 118 sides of the incision 120 may remain spaced apart after cinching of the belt 108 (i.e. may be brought to a partially closed position). This may occur, for example, in cases where a patient has abdominal swelling.

In the example shown, as zip ties automatically lock when tightened, the belt 108 is automatically and temporarily secured in the cinched configuration, to hold the incision in the partially closed position. In alternative examples, a separate securing step may be carried out. For example, in cases where a cord or cable is laced between first connector and second connector, the cord or cable may be tied to secure the belt in the cinched configuration.

As can be seen in FIGS. 8 and 9, as the first 132a and second 132b sets of loops extend upwardly away from the plates 134a, 134b, when the first belt lock 130a and second belt lock 130b are positioned on opposed sides 116, 118 of the incision 120, the first 132a and second 132b sets of loops are spaced away from the patient's skin. As such, when the cinching devices 126, 128 are secured to the first connector 122 and second connector 124, the cinching devices 126, 128, are also spaced away from the patient's skin, and pass over the incision 120 without touching the incision 120. This may be beneficial, as the cinching devices 126, 128 may generally not irritate the incision 120 or cause any further damage to the incision 120. In some examples, the height of the loops 132a may be between about 3 cm and about 5 cm from the base of the first connector 122. In some examples, the height of the loops 132a may be about 2 cm from the base of the first connector 122.

As can be seen in FIGS. 8 and 9, in this example, gauze 148 is placed adjacent the incision 120 on the opposed sides 116, 118 of the incision 120. In alternative examples, the gauze may be omitted.

Although not shown in the Figures, during the period of time that the device 102 is in place on the patient, the cinching devices 126, 128 can be further tightened, to bring the incision further towards a closed position. For example, the cinching devices 126, 128 may be tightened periodically as abdominal swelling decreases.

The device 102 may be removed from the patient at any suitable time, for example at the time of definitive closing of the incision 120. The device 102 may be removed, for example, by cutting the zip ties. This may optionally be done at the bedside, without any anesthesia or special instruments.

In some examples, the device may be applied without creating any additional wounds in the patient's abdomen. For example, in the method shown in FIGS. 4 to 10, the device has been applied without being stitched to the patient's abdomen.

In some examples, the incision 120 may be definitively closed with the device 102 still secured to the patient, and the device may be removed after the incision 120 is definitively closed. Leaving the device secured to the patient may facilitate suturing of the incision.

In alternative examples, the device 102 may be removed from the patient prior to definitive closing of the incision 120.

Figure 10:
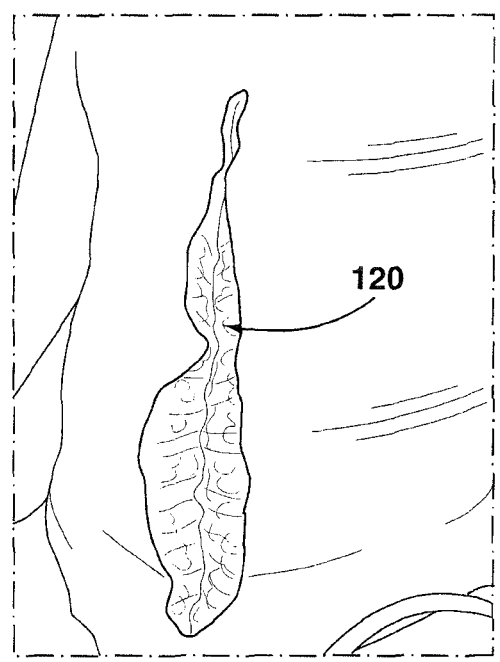

FIG. 10 shows the incision 120 after the sutures in the fascia are tightened to definitively close the incision 120 and the device 102 is removed. In this example, the subcutaneous tissue is purposely left open, to prevent abscess formation.

Referring now to FIGS. 14A to 14D, another example first connector 1422 is shown. For simplicity only the first connector 1422 is shown and described. The corresponding second connector may be similar or identical to the first connector 1422.

Referring to FIGS. 14A and 14B, the first belt lock 1430a of the first connector 1422 includes a single plate 1434a, and a rod 1450a. The plate 1434a has a pair of slots 1452a, 1454a, extending lengthwise along the plate 1434a transversely through the plate 1434a. The rod 1450a is sized so that it cannot fit through the second slot 1454a. In the example shown, the rod 1450a has a diameter larger than the width of the second slot 1454a.

Figure 14C:
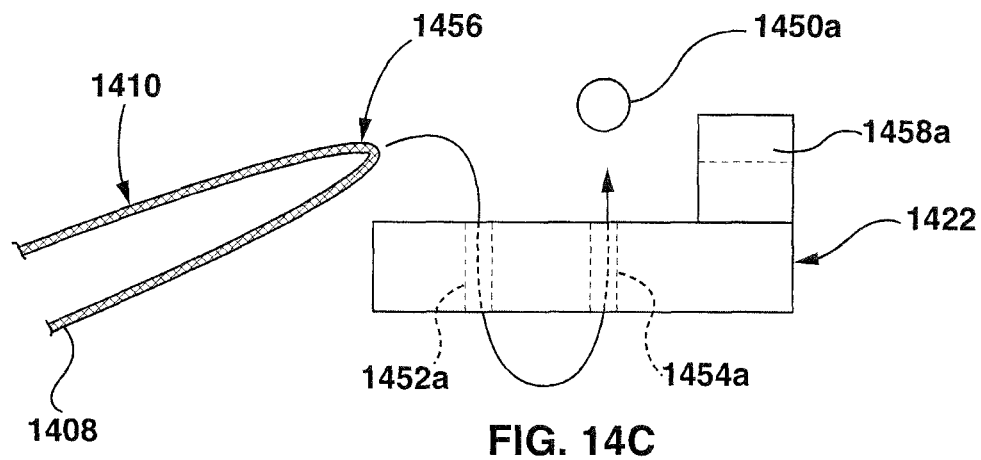
FIG. 14C is a schematic side view showing a belt being connected to the first connector of FIGS. 14A and 14B.
Figure 14D:
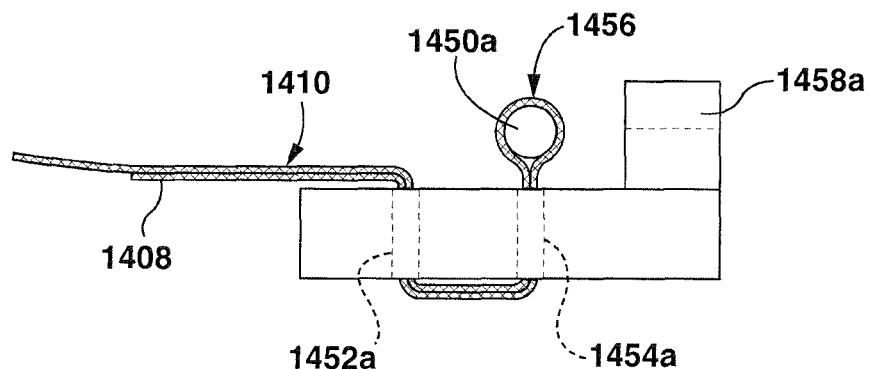
FIG. 14D is a schematic side view showing the belt and first connector of FIG. 14C secured together with a rod of the first connector.

Referring to FIGS. 14C and 14D, in order to secure the first end portion 1410 of the belt 1408 to the first connector 1422, the first end portion 1410 may be folded over to form a loop 1456 (also referred to as a fold 1456). The loop may then be threaded downwardly through the first slot 1452a, and back upwardly through the second slot 1454a, as shown in FIG. 14C. The rod 1450a may then be inserted through the loop 1456a, and the first end portion 1410 of the belt 1408 may be pulled taut against the rod 1450a, to secure the first end portion 1410 of the belt 1408 to the first connector 1422. This may be repeated with the second end of the belt and the second connector (not shown).

Referring back to FIGS. 14A and 14B, in this example, the second connector 1422 includes a block 1458a that is secured to the plate 1434a (e.g. with one or more fasteners such as screws or with an adhesive), and extends lengthwise along the plate 1434a. The block 1458a includes a set of channels 1459a formed widthwise therethrough. The channels 1459a form a set of loops through which cinching devices (not shown) may be threaded, as described above with respect to FIGS. 1 to 13. In this example, the channels 1459a span the majority of the length 1444a of the plate 1434a, which may allow for cinching devices to be spread generally evenly along the length of the plate 1434a. For example, a respective zip tie may be threaded through each channel 1459a, so that the device includes three zip ties spaced generally equally along the length 1444a of the plate 1434a. Alternatively, two zip ties may be threaded through each channel 1459a, at opposed ends of each channel, so that the device includes six zip ties spaced generally equally along the length 1444a of the plate 1434a.

In alternative examples (not shown), the block 1458a may be integral with the plate 1434a.

Figure 15A:
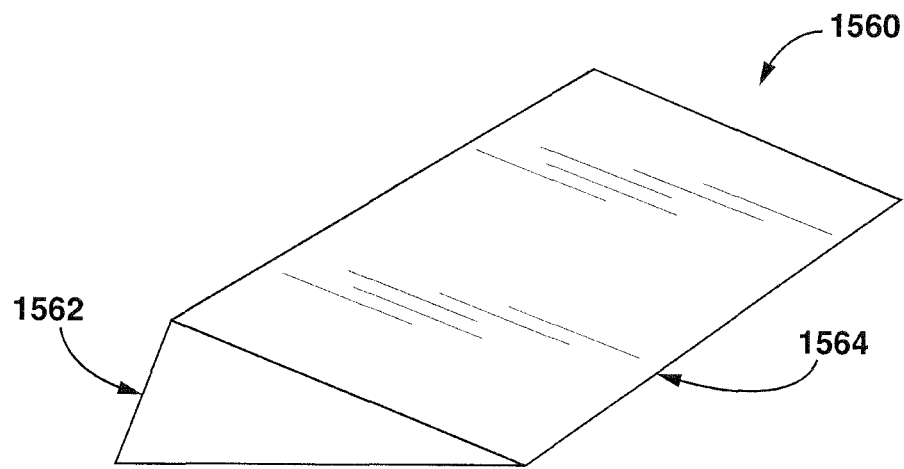
FIG. 15A is a perspective view of a shim.
Figure 15B:
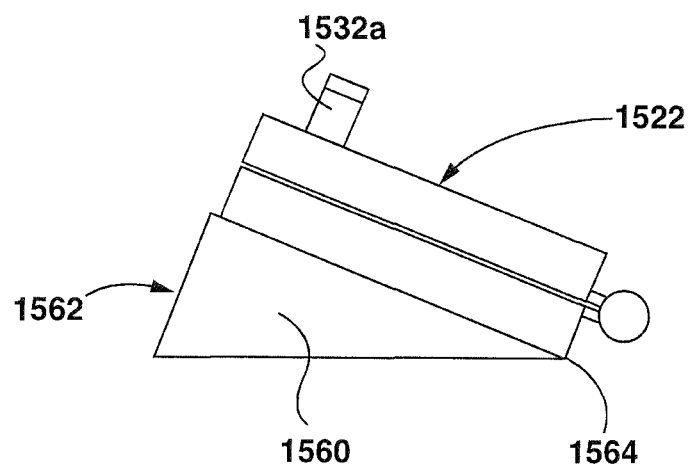
FIG. 15B is a side elevation view of the shim of FIG. 15A secured to a connector similar to the first connector of FIG. 1.

Referring now to FIG. 15A, a shim 1560 may be used with any of the connectors described herein. In FIG. 15B, the shim 1560 is shown secured to a first connector 1522 similar to that of FIG. 1. In use, a similar shim may be secured to a second connector (not shown).

In the example shown, the shim 1560 is generally in the form of a wedge, and includes a tall side 1562 and a short side 1564. The shim 1560 is secured to the first connector 1522 so that the tall side underlies the loops 1532a of the first connector 1522. In use, the shim 1560 elevates the loops 1532 of the first connector 1522, so that the first connector 1522 is inclined with respect to the patient's abdomen.

In use, as the cinching devices (e.g. zip ties) are cinched, the shim 1560 is forced downwardly against the patient's body as the first connector 1522 and second connector (not shown) are cinched towards each other. This downward force may further stabilize the abdomen (E.g. the rectus abdominal muscle), and help to prevent or reduce or minimize loss of the abdominal domain.

In the example shown, the shim 1560 is secured to the first plate 1534a of the first connector 1522 with a single screw (not shown). Optionally, the screw may be loosened or removed, so that the shim 1560 may be pivoted to position the short side 1564 to underlie the loops 1532a. This may be done, for example, to apply forces in other directions or at other positions, depending on the patient's injury and anatomy.

In alternative examples, the shim may be removable from the first connector in another manner (e.g. a removable clip instead of a screw), or may be permanently secured to the first connector (e.g. they may be integral).

Figure 16:
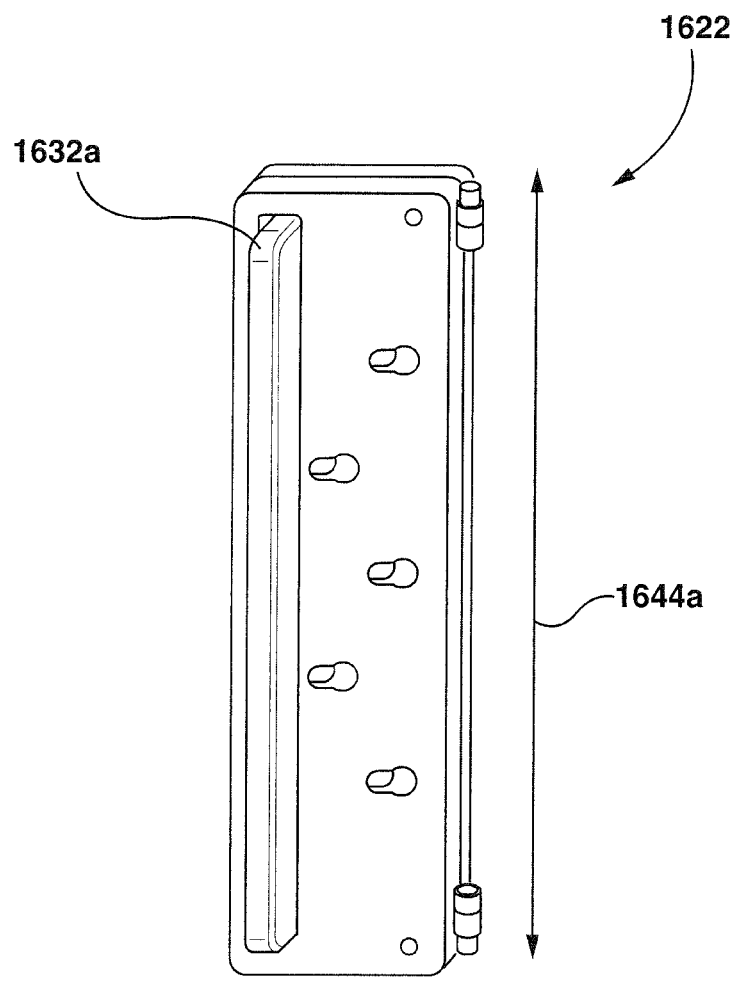
FIG. 16 is a top plan view of another first connector.

Referring now to FIG. 16, another example first connector 1622 is shown. For simplicity only the first connector 1622 is shown and described. The corresponding second connector may be similar or identical to the first connector 1622. In this example, the first connector 1622 is similar to the first connector 122 of FIG. 1, but includes a single loop 1632a, which spans a majority of the length 1644a of the first connector 1622. Similarly to the first connector 1422 of FIGS. 14A to 14D, this may allow for cinching devices to be spread generally evenly along the length of the plate 1434a.

In any of the above examples, the device may be used in combination with other devices and methods for management of an open abdomen. For example, various devices and methods for containment and protection of the abdominal contents may be used together with the devices and methods described herein. Such devices and methods may include, for example, negative pressure therapy systems such as those commercially available under the brand name ABThera™, and stitches.

EXAMPLE

Example 1

A study was done to test the device of FIGS. 1 to 10 in a pig model.

Materials and Methods

Preparation: A total of six (n=6) pigs were used in this study. The animals arrived at the animal facility between 3-5 days before the day of procedure. All animals fasted overnight before the procedure. Each pig was anesthetized with ketamine (20 mg/kg, 6-7 mL)+Xylazine (2 mg/kg, 3-3.5 mL)+Atropine Sulphate (1 mg/25 kg, 1-2 mL), intramuscularly using a 21 g needle, once pre-op as pre-medication; Isoflurane 2-5% inhaled for maintenance throughout procedure. An IV line was placed in the ear vein using a 20 g angiocatheter, and the pigs were maintained on saline throughout the procedure. Once anesthetized, the pigs were intubated and maintained on a ventilator (10 ml/kg) at 2-3% Isoflurane for the duration of the procedure. Animals were monitored via jaw tone, pulse oximetry, ECG, intra-tracheal pressure, and intra-arterial pressure. Once the pig was at a surgical plane of anesthesia the procedure commenced.

Surgical Procedure: Initially, the abdominal wall was punctured to the left of the midline with an intravenous catheter. This catheter was used to measure the intra-abdominal pressure through the experiment. A metric ruler was used to measure the length of the laparotomy, as well as to mark 3 sites on the abdominal wall: (Site 1) 2 cm below the xyphoid, (Site 2) umbilicus, and (site 3) 2 cm above the symphysis. Afterwards, a laparotomy was performed. Intra-abdominal pressure was measured after the laparotomy. A stitch was passed through the edges of the laparotomy at each one of the previously marked sites. Each stitch formed a 10 cm diameter loop which was connected to a digital scale. The pound force necessary to bring the edges of the laparotomy to the midline was measured at each site.

The device shown in FIGS. 1 to 10 was applied to each pig as described above. Briefly, connectors as shown in FIGS. 3A to 3D were placed on each side of the abdominal wall on top of the rectus abdominal muscle, and a belt consisting of an elastic bandage was wrapped tautly around the torso of each pig and connected to the connectors. Two zip ties were connected to the connectors and tightened until the edges of the laparotomy were brought together at the midline. The intra-abdominal pressure was measured in sequence. Finally, the device was removed, the laparotomy was closed with running sutures, and the intra-abdominal pressure was measured again. All measurements were performed in triplets.

Statistical Analysis: Data is reported as mean±SEM. Data was analysed using Analysis of Variance (ANOVA) and Post-test Tukey, with statistical software GraphPad Prism 6® Software, Inc. (La Jolla, Calif.). Statistical significance was set at $p<0.05$.

Results

The animals weighed an average of 31.9±0.86 Kg. The distance from the xyphoid to the pubis was 36.42±1.3 cm, and the length of the laparotomy incision was slightly shorter at 31.67±1.6 cm. Baseline intra-tracheal pressure was taken before performing the abdominal incision to assess the effect of the abdominal binder on that physiologic variable. Baseline intra-tracheal pressure was 12.63±0.91 cm/$H_2O$. Baseline intra-abdominal pressure was also recorded before performing the laparotomy incision. Mean intra-abdominal pressure at baseline was 0.98±0.20 mmHg. There were no statistically significant differences between the aforementioned values among the animals ($p>0.05$).

Figure 11:
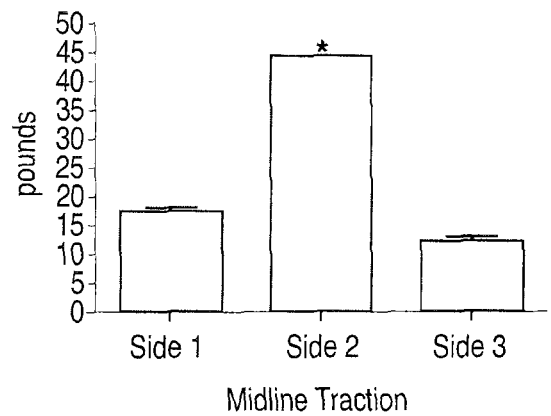
FIG. 11 is a bar graph showing the re-approximation force that was required to bring the edges of the abdominal incision to the midline at three sites.

The re-approximation force (pounds) required to bring the edges of the abdominal incision to midline varied between the three sites where it was assessed (FIG. 11). As expected, site number 2 had significantly higher values compared to sites 1 and 3, because of a larger gap between the edges of the incision; *$p<0.05$.

Site 1: 17.44±0.46 Lb
Site 2: 44.14±0.01 Lb
Site 3: 12.11±0.75 Lb

Data With the Device in Place: Tightening of the zip ties effectively brought the edges of the abdominal wall incision to the midline in all 6 animals.

Figure 12:
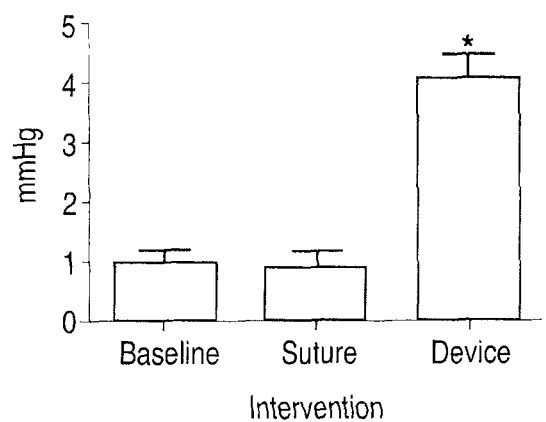
FIG. 12 is a bar graph showing intra-abdominal pressure compared to baseline values, and after the abdominal incision was closed by suture, with the device in place and cinched tightly.

The device significantly increased intra-abdominal pressure compared to baseline values, and after the abdominal incision was closed by suture; *$p<0.05$ (FIG. 12). This demonstrates that the device effectively exerted pressure over the entire abdominal wall of the animal.

Figure 13:
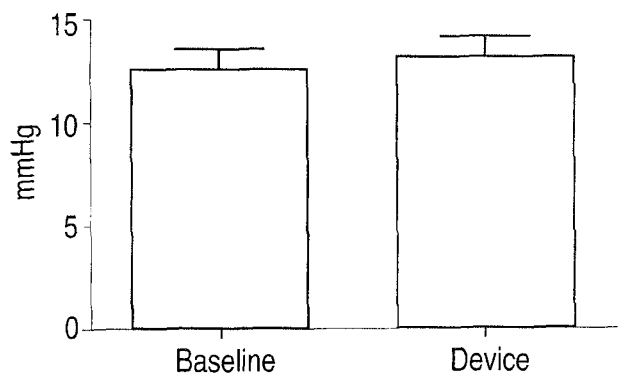
FIG. 13 is a bar graph showing intra-tracheal pressure compared to baseline values.

The intra-tracheal pressure did not increase despite the increase in intra-abdominal pressure with the device in place, compared to baseline (FIG. 13). Moreover, the average heart rate and the oxygen saturation remained unchanged with the device in place; respectively 88±3 bpm and 97±2%.

The above data demonstrates that device and methods described herein may effectively aid in definitively closing an abdominal wall incision, and may provide enough force for abdominal wall closure.

The above data also demonstrates that abdominal closure may be obtained without any derangement of the respiratory and cardiovascular status of the animals.

Moreover, the force exerted on the abdominal wall by the device provoked an overall increase in intra-abdominal pressure. This demonstrates that the device may stabilize the abdominal wall musculature as a whole.

Example 2

A study was done to test the device of FIGS. 1 to 10 in a human model.

Materials and Methods

A prospective single center randomized controlled trial was conducted to assess the efficacy the device of FIGS. 1 to 10 in progressive closure of the open abdomen. The device was used in conjunction with negative pressure wound therapy (Device Group), versus negative pressure alone (Control Group). The trial commenced in June 2015. The device was applied as described above with respect to FIGS. 4 to 10. Briefly, the device was applied at each patient's bedside, without any surgical instruments or anesthesia, and without removing the negative pressure wound therapy. The skin on each side of the incision was protected with adhesive padded tape. The belt was passed around the patient's back. The end portions of the belt were secured to two respective connectors of the device, one on each side of the incision. The connectors were positioned on top of the previously placed padded tape on each side of the incision. Zip ties were passed through loops on each connector, bridging the incision, without contact to the skin or the negative pressure dressing. The zip ties were tightened to obtain tension. The zip ties were subsequently progressively tightened up in follow up assessment. The zip ties were later removed by cutting them with scissors at the bedside.

Results

Figure 17A:
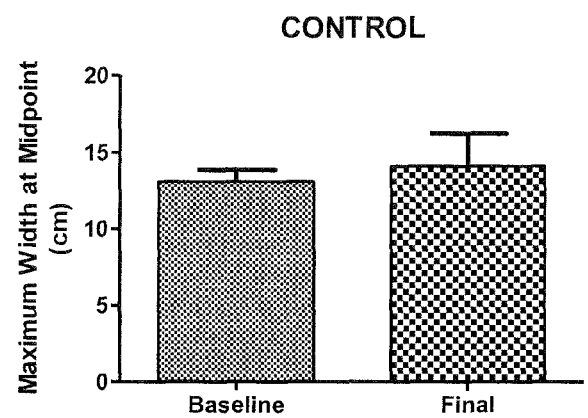
FIG. 17A is a bar graph showing the width of the abdominal wall defect at the time of closure compared to the initial width in the Control Group.
Figure 17B:
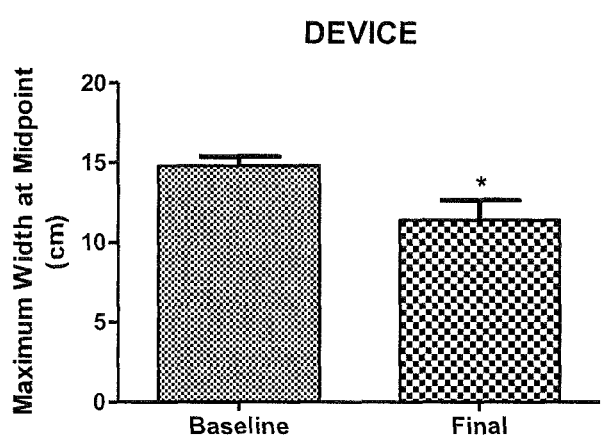
FIG. 17B is a bar graph showing the width of the abdominal wall defect at the time of closure compared to the initial width in the Device Group.
Figure 18A:
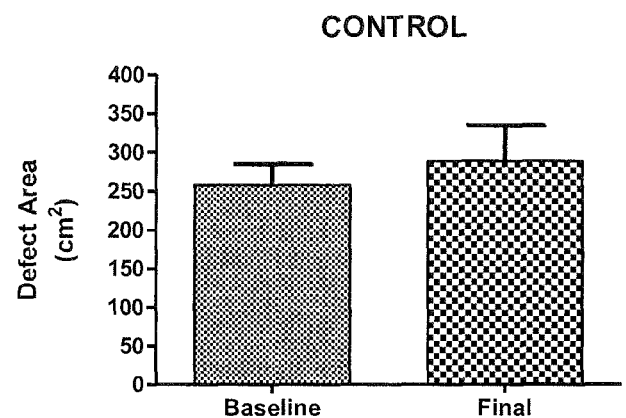
FIG. 18A is a bar graph showing the area of the abdominal wall defect at the time of closure compared to the initial area in the Control Group.
Figure 18B:
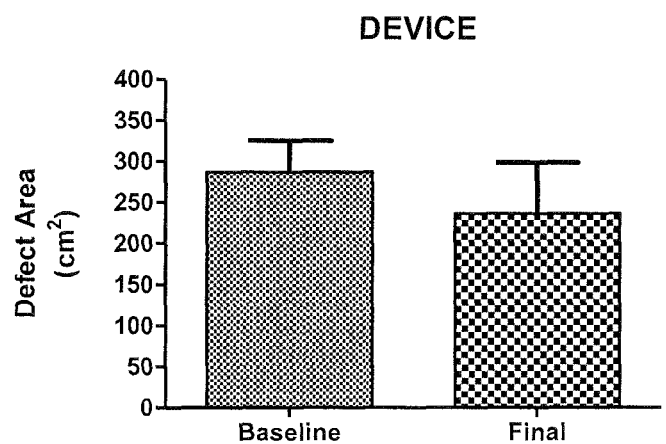
FIG. 18B is a bar graph showing the area of the abdominal wall defect at the time of closure compared to the initial area in the Device Group.

The total number of patients screened was 17. Of these 17, 5 patients did not provide consent, and two presented with enterocutaneous fistulae, hence were not enrolled. Therefore, 10 patients were randomized; 5 in each group. The mean age of the patients was 58.6±10.8 years in the control group, and 55.8±11.6 years in the device group ($p>0.05$). There was no statistically significant difference in the body mass index (BMI) between the Control Group and the Device Groups (26.5±3.2 vs. 28.2±2.5, Control Group vs. Device Group). There was no statistically significant difference in APACHE II score between the groups (22.3±2.6 vs. 20±2.8, Control Group vs. Device Group). Lactate levels up to 72 h were not statistically significant different between the groups (2.2±0.4 mmol/L vs. 1.9±1.4 mmol/L, Control Group vs. Device Group). In the Device Group, the device and the negative pressure therapy remained in use on the abdomens for 3.8±1.2 days; in the Control Group, the negative pressure therapy remained in use on the abdomens for 3.4±2.07 days ($p>0.05$). The initial widths of the abdominal wall defect measured at the widest point were 13.1±0.8 cm vs. 14.8±0.6 cm ($p>0.05$), control vs. device. The initial areas of the abdominal wall defects were 257.9±26.2 $cm^2$ vs. 287.3±38.2 $cm^2$, control vs. device. There was no statistically significant difference in the width of the abdominal wall defect at the time of closure compared to the initial width in the Control Group (14.1±2.1 cm vs. 13.1±0.8 cm ($p>0.05$)), as shown in FIG. 17A. In the Device Group there was a significant reduction in the width of the abdominal wall defect at the time of closure compared to the initial width (11.4±1.2 cm vs. 14.8±1.2 cm ($p<0.05$), as shown in FIG. 17B. The difference in the area of the abdominal wall defect at the time of closure, compared to baseline, did not differ significantly in each respective group. See FIGS. 18A and 18B. However, although not statistically significant, the area did increase in the control group and did decrease in the device group, compared to baseline; respectively (288.4±46 $cm^2$ vs. 236.1±62.4 $cm^2$). Four patients in the device group underwent primary fascial closure; 3 patients in the control group underwent primary fascial closure. Only one patient in the device group required mesh to be stitched to the skin to assist closure, whereas 3 patients in the control group underwent abdominal closure with mesh. One patient in the Control Group also required component separation (additional incisions and surgery to facilitate closure). There were no complications related to the device, and no occurrences of abdominal compartment syndrome. The skin surface had no signs of injury in any of the patients in which the device was applied. Two patients in the Device Group underwent an ostomy, and one patient in the Control Group underwent an ostomy. There were 3 deaths: two in the Control Group and one in the Device Group. All deaths occurred weeks after the abdomens were closed, and were not related to the abdominal closure.

While the above description provides examples of one or more processes or apparatuses, it will be appreciated that other processes or apparatuses may be within the scope of the accompanying claims.

The invention claimed is:

1. A device for management of an open incision in a patient, the device comprising:
   a) a belt having a first end portion and an opposed second end portion, the belt positionable to extend partially around the patient in a taut configuration with the first end portion and the second end portion positioned on opposed sides of the incision;
   b) a first connector and a second connector, the first connector comprises a first belt lock holding the first end portion and the second connector comprises a second belt lock holding the second end portion, the first belt lock comprises a clamp adapted to hold the first end portion and the second belt lock comprises a clamp adapted to hold the second end portion, the first connector and second connector positionable adjacent to each other on the opposed sides of the incision when the belt is positioned around the patient in the taut configuration; and
   c) at least one cinching device connected to and extending between the first connector and the second connector, the cinching device positionable to extend over the incision when the first connector and second connector are positioned adjacent each other on opposed sides of the incision, the cinching device adjustable to cinch the first end portion and second end portion towards each other to hold the incision in an at least partially closed position.

2. The device of claim 1 wherein the at least one cinching device is adapted to collectively apply 11.36 to 17.9 pounds of tension between the connectors.

3. The device of claim 1 configured to manage an incision in the abdomen of the patient.

4. The device according to claim 1, wherein the clamp comprises a first plate hingedly connected to a second plate, the clamp movable between an open position and a closed position.

5. The device according to claim 4, wherein the first belt lock and the second belt lock each comprise a gripping mechanism for holding the first end portion and the second end portion, respectively.

6. The device according to claim 5, wherein the gripping mechanism comprises a plurality of spikes extending upwardly from the first plate, and a plurality of openings in the second plate configured to receive the plurality of spikes when the clamp is in the closed position.

7. A method for management of an incision in a patient, the method comprising:
   a) positioning a belt to extend partially around the patient from a first position on a first side of the incision, around a portion of the patient, to a second position on a second side of the incision, in a taut configuration;
   b) securing a first connector to a first end portion of the belt and securing a second connector to a second end portion of the belt, the first connector comprises a first belt lock holding the first end portion and the second connector comprises a second belt lock holding the second end portion, the first belt lock comprises a clamp adapted to hold the first end portion and the second belt lock comprises a clamp adapted to hold the second end portion, and where the first and second connectors are adapted to connect to a cinching device;
   c) cinching the belt to a cinched configuration to bring the first side of the incision and second side of the incision towards each other; and
   d) temporarily securing the belt in the cinched configuration, to temporarily hold the incision in an at least partially closed configuration.

8. The method of claim 7, further comprising: prior to step c), positioning the first connector on the first side of the incision, and positioning the second connector on the second side of the incision adjacent to the first connector.

9. The method of claim 7, further comprising: prior to step c), configuring a cinching device between the first connector and second connector so that the cinching device extends between the first connector and the second connector and over the incision.

10. The method of claim 9, wherein step c) comprises cinching the cinching device.

11. The method of claim 10 wherein step d) is carried out automatically upon cinching the belt.

12. The method of 7 further comprising e) tightening the belt periodically.

13. The method of claim 7 wherein step c) comprises applying 11.36 to 17.9 pounds of tension between the connectors.

14. The method of claim 13 wherein the incision is in the abdomen of the patient.

15. The method of claim 14 wherein the force exerted on the abdominal wall of the patient provokes an overall increase in intra-abdominal pressure.

16. The method of claim 7 comprising bringing the edges of the incision together to meet.

17. The method according to claim 7, wherein the clamp comprises a first plate hingedly connected to a second plate, the clamp movable between an open position and a closed position.

18. The method according to claim 17, wherein the first belt lock and the second belt lock each comprise a gripping mechanism for holding the first end portion and the second end portion, respectively.

19. The method according to claim 18, wherein the gripping mechanism comprises a plurality of spikes extending upwardly from the first plate, and a plurality of openings in the second plate configured to receive the plurality of spikes when the clamp is in the closed position.

20. A kit of parts for a device for management of an open incision in a patient, the kit of parts comprising:
   a) a belt having a first end portion and an opposed second end portion, the belt positionable to extend partially around the patient in a taut configuration with the first end portion and the second end portion positioned on opposed sides of the incision;
   b) a first connector and a second connector, the first connector comprises a first belt lock holding the first end portion and the second connector comprises a second belt lock holding the second end portion, the first belt lock comprises a clamp adapted to hold the first end portion and the second belt lock comprises a clamp adapted to hold the second end portion, the first connector and second connector positionable adjacent to each other on the opposed sides of the incision wherein the first connector is adapted to be connected to the first end portion and the second connector is adapted to be connected to the second end portion; and c) at least one cinching device adapted to be connected to the first and second connectors, the cinching device configured to be positionable to extend over the incision when connected to the first connector and second connector and when the first connector and second connector are positioned adjacent each other on opposed sides of the incision with the belt being positioned around the patient in the taut configuration, the cinching device being adjustable to cinch the first end portion and second end portion towards each other to hold the incision in an at least partially closed configuration.

21. The kit of parts of claim 20, wherein any one of components a, b or c is provided unassembled from any others of the components a, b or c.

22. The kit of parts of claim 20 wherein any one of components a, b or c is provided assembled to any others of the components a, b or c.

23. The kit of parts of claim 20 wherein the cinching device is adapted to apply 11.36 to 17.9 pounds of tension between the connectors.

24. The kit of parts of claim 20 wherein the assembled device is configured to manage an incision in the abdomen of the patient.

25. The kit according to claim 20, wherein the clamp comprises a first plate hingedly connected to a second plate, the clamp movable between an open position and a closed position.

26. The kit according to claim 25, wherein the first belt lock and the second belt lock each comprise a gripping mechanism for holding the first end portion and the second end portion, respectively.

27. The kit according to claim 26, wherein the gripping mechanism comprises a plurality of spikes extending upwardly from the first plate, and a plurality of openings in the second plate configured to receive the plurality of spikes when the clamp is in the closed position.

* * * * *

UNITED STATES PATENT AND TRADEMARK OFFICE
CERTIFICATE OF CORRECTION

PATENT NO. : 10,524,793 B2
APPLICATION NO. : 15/550444
DATED : January 7, 2020
INVENTOR(S) : João Baptista De Rezende Neto Page 1 of 1

It is certified that error appears in the above-identified patent and that said Letters Patent is hereby corrected as shown below:

In the Claims

Column 16, Line 9, Claim 7, delete "where" and insert -- wherein --

Column 16, Line 30, Claim 12, after "of" insert -- claim --

Column 16, Line 32, Claim 13, delete "claim 7" and insert -- claim 7, --

Signed and Sealed this
Fifth Day of May, 2020

Andrei Iancu
*Director of the United States Patent and Trademark Office*